US012171464B2

United States Patent
Kumar et al.

(10) Patent No.: US 12,171,464 B2
(45) Date of Patent: Dec. 24, 2024

(54) FIXING DEVICE

(71) Applicant: Lincotek Trento S.p.A., Pergine Valsugana (IT)

(72) Inventors: Mukesh Kumar, Pergine Valsugana (IT); Stefano Rappo, Pergine Valsugana (IT); Massimiliano Tomaselli, Pergine Valsugana (IT); Gianluca Zappini, Pergine Valsugana (IT); Federico Scarpulla, Pergine Valsugana (IT); Giacomo Erani, Pergine Valsugana (IT)

(73) Assignee: LINCOTEK TRENTO S.P.A., Pergine Valsugana (IT)

( * ) Notice: Subject to any disclaimer, the term of this patent is extended or adjusted under 35 U.S.C. 154(b) by 0 days.

(21) Appl. No.: 17/989,029

(22) Filed: Nov. 17, 2022

(65) Prior Publication Data

US 2023/0355278 A1    Nov. 9, 2023

(30) Foreign Application Priority Data

May 6, 2022   (IT) .......................... 102022000009407

(51) Int. Cl.
*A61B 17/84*    (2006.01)
*A61B 17/68*    (2006.01)

(52) U.S. Cl.
CPC .................. *A61B 17/686* (2013.01)

(58) Field of Classification Search
CPC ........................................... A61B 17/84–8695
See application file for complete search history.

(56) References Cited

U.S. PATENT DOCUMENTS

| | | | |
|---|---|---|---|
| 4,038,703 A * | 8/1977 | Bokros | A61F 2/06 623/2.38 |
| 6,790,233 B2 * | 9/2004 | Brodke | A61L 27/365 623/17.11 |
| 8,163,031 B2 * | 4/2012 | Truckai | A61B 17/686 623/23.73 |
| 8,257,395 B2 * | 9/2012 | Bhatnagar | A61B 17/7002 606/907 |
| 8,734,520 B2 * | 5/2014 | Zwirkoski | A61B 17/686 623/17.16 |
| 8,992,537 B1 * | 3/2015 | McDonnell | D04C 1/06 606/86 R |
| 2006/0241623 A1 * | 10/2006 | Lim | A61B 17/8625 606/265 |
| 2019/0343565 A1 * | 11/2019 | Tempco | A61B 17/863 |
| 2019/0343567 A1 * | 11/2019 | Tempco | B33Y 80/00 |
| 2020/0022817 A1 * | 1/2020 | Crossgrove | A61B 17/863 |
| 2020/0323574 A1 * | 10/2020 | Picha | A61B 17/742 |
| 2020/0390944 A1 * | 12/2020 | Williams | A61F 2/30721 |
| 2021/0153911 A1 * | 5/2021 | Stuart | A61B 17/869 |
| 2022/0104858 A1 * | 4/2022 | Ball | A61B 17/8635 |

* cited by examiner

*Primary Examiner* — Eduardo C Robert
*Assistant Examiner* — Steven J Cotroneo
(74) *Attorney, Agent, or Firm* — Tutunjian & Bitetto, P.C.

(57) ABSTRACT

The present invention relates to a fixing device, particularly suitable for being engaged in a suitable bone site in the context of regenerative and/or reconstructive surgery, such as for example vertebral surgery or trauma surgery.

21 Claims, 6 Drawing Sheets

FIXING DEVICE

BACKGROUND

Technical Field of the Invention

The present invention relates to a fixing device, particularly suitable for being engaged in a suitable bone site, for example in the context of regenerative and/or reconstructive surgery, such as for example vertebral surgery or trauma surgery. More in detail, this fixing device can comprise a bone and/or pedicle screw and is possibly made by means of a three-dimensional or 3D printing method, such as for example additive manufacturing.

Description of Related Art

As is known, the fixing devices which are most commonly used in the medical field are screws which can be pedicle screws, often used for the treatment of vertebral surgery, or simple bone screws, which can be used in trauma surgery.

Typically, in the context of vertebral surgery these fixing devices are used together with other metal elements, especially plates or bars, for the stabilization of the spine, where stabilization means the application of one or more elements or devices in order to maintain strong and firm two or more adjacent vertebrae. This procedure is necessary, for example, in the case of vertebral spondylosis, which can be malformative, traumatic or degenerative.

In this context, the fixing devices must be able to adapt to the different directions that the bars or plates may take following the vertebral column to re-establish the correct three-dimensional alignment of the affected vertebrae.

Considering, for example, a pedicle screw, it is used by exploiting the vertebral pedicle, that is the protruding end of the vertebra in the shape of a hollow cylinder covered externally by cortical tissue with spongy tissue inside. Its size and orientation vary according to the various segments of the vertebral column and, therefore, various lengths of the pedicle screw are provided for the stabilization of the various segments.

Furthermore, it is necessary to have a "movable head" in order to be able to insert the screw in the desired direction; this mobility is obtained by assembling two physically separate components with a semi-spherical joint: the screw, inserted in the vertebral peduncle, and the head, on which the bar or external plate is locked.

In general, in the daily post-operative period, the implanted fixing devices must withstand the stresses produced by the body, which is in a condition of bone resorption. In order to improve bone fixation capabilities, the external surface of the screw is sometimes coated with a thin layer of titanium and/or hydroxyapatite particles, applied by plasma spray techniques, which increases surface roughness and osseointegration capabilities of the device. Given the small size of the device, this layer has in any case very limited thicknesses, and therefore the increase in roughness and primary fixing capacity is limited.

It is therefore not uncommon, in the fixing devices provided by the prior art, to see a loosening in the grip of the device, a screw coming out of its seat or a disassembly of the screw with respect to the head due to mechanical strains (torsion and bending) transferred from the fixation bars or plates, resulting in failure of internal fixation.

It can therefore be understood that the mechanical strength, the robustness of the assembly of the two components and the adhesion with the bone seat of the fixing device are the key factors for the success of the surgical operation.

Often, these fixing devices generate considerable difficulty in osseointegration, significantly complicating and slowing down the patient's post-operative recovery phase.

It is therefore necessary to design and manufacture a fixing device which allows to overcome the disadvantages listed in the state of the prior art.

SUMMARY OF THE INVENTION

The technical task of the present invention is to improve the state of the prior art concerning fixing devices, and more in detail, inherent to fixing devices suitable for being engaged in specific bone seats, for example, in the context of regenerative surgery and/or reconstructive, such as spinal surgery or trauma surgery.

Within this aim, it is an object of the present invention to provide a fixing device which has high mechanical resistance to torsion and bending and, at the same time, allows the use of a greater volume of material useful for the adaptation or integration of the bone tissue and which, therefore, allows a better osseointegration when compared to the fixing devices of same sizes produced according to the state of the prior art.

Another object of the present invention is to provide a fixing device which has an optimized cross-section as a function of the mechanical strength and volume of material to be used for the adaptation or integration of the bone tissue.

Still another object of the present invention is to provide a fixing device which can be manufactured in a simple and quick way, for example, by means of a single manufacturing step, so as to avoid complicated assembly operations and any risks of disassembly during clinical use.

This aim and these objects are achieved by a fixing device according to the present application.

The present application refers to preferred and advantageous embodiments of the invention.

BRIEF DESCRIPTION OF THE DRAWINGS

Other characteristics and advantages of the invention will be more evident from the description of an embodiment of a fixing device, illustrated by way of example in the accompanying drawings in which.

In the accompanying drawings, identical parts or components are indicated by the same reference numbers.

DETAILED DESCRIPTION OF THE INVENTION

With reference to the attached figures, the number 1 generally indicates a fixing device according to a non-limiting embodiment of the present invention.

The fixing device 1 is particularly, but not exclusively, suitable for use in the medical field, and in particular, for example, in the context of regenerative and/or reconstructive surgery, such as for example vertebral surgery or trauma surgery.

Figure 12:
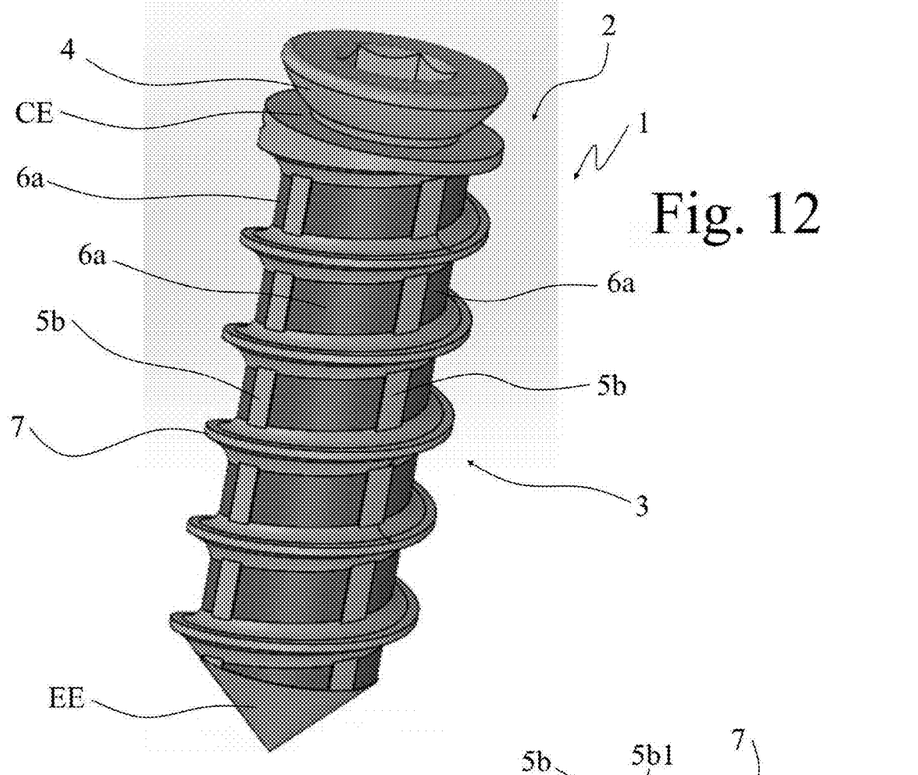
FIG. 12 is a perspective view of a fixing device according to a still further embodiment of the present invention.

In this case, the fixing device 1 can advantageously be a pedicle screw (for example illustrated in FIG. 1) or a bone or trauma screw (for example illustrated in FIG. 12).

The fixing device 1 according to the present invention comprises an anchoring body 2, which constitutes, for example, a portion extending along a first direction or longitudinal direction of the fixing device 1 and can be engaged, in use, in a bone seat, and a head portion 4.

The anchoring body 2 is constituted, in at least one version of the invention, by a constraint portion 3 (for example, in a conformation to allow a physical constraint), an apical engaging end EE and a distal end CE, the latter connecting with the head portion 4.

Figures 4, 5:
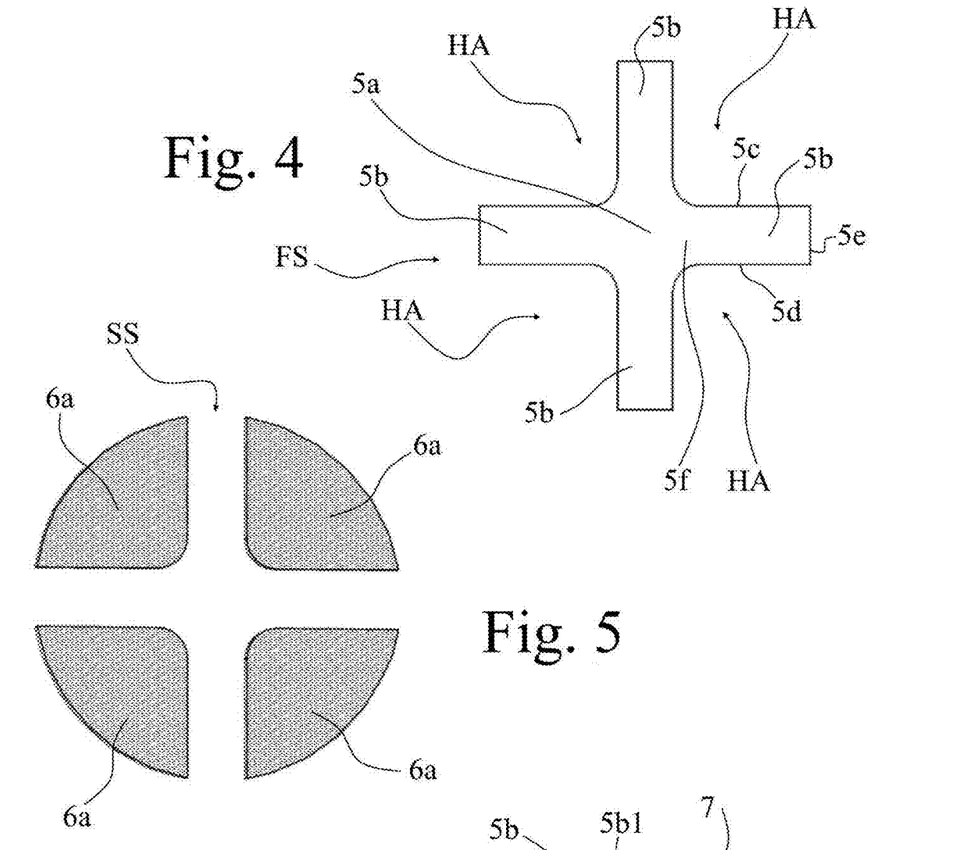
FIG. 4 is a cross-sectional view of a component (for example of the core or main body) of the fixing device according to the embodiment shown in FIG. 1.
FIG. 5 is a cross-sectional view of another component (for example of the complementary or filling structure and/or volume) of the fixing device according to the embodiment shown in FIG. 1.

In particular, the constraint portion 3 includes a core or main body 5 delimiting a first cross-section area FS (for example illustrated in FIG. 4).

The constraint portion 3, in at least one version of the invention, preferably also comprises a complementary or filling structure and/or volume 6 delimiting a second cross-section area SS (for example illustrated in FIG. 5).

Figure 6:
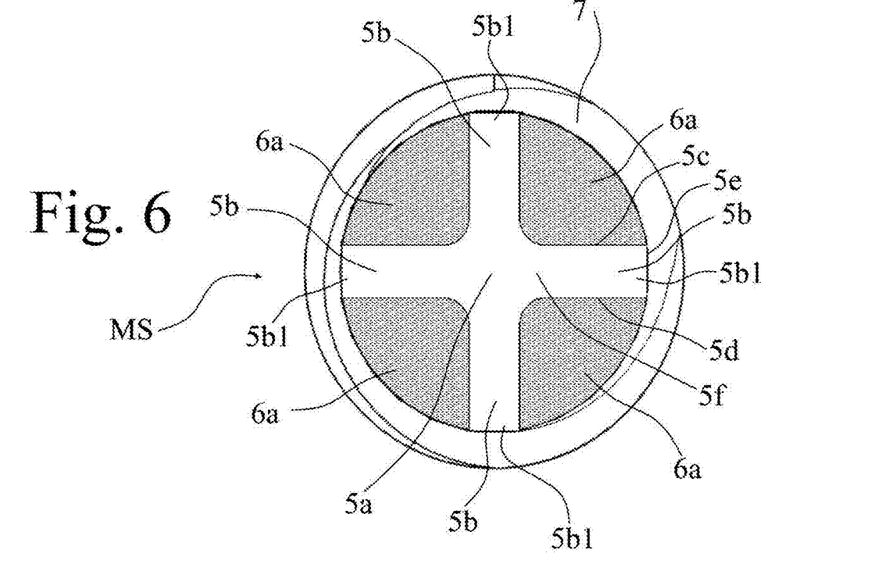
FIG. 6 is a cross-sectional view of the fixing device according to the embodiment shown in FIG. 1, FIGS. 7, 8 and 9 each show a cross-sectional view of a fixing device according to an alternative embodiment of the present invention.

The cross-section SS defines, with the first cross-section FS, an overall cross-section MS for the constraint portion 3 (for example illustrated in FIG. 6).

In other words, the overall cross-section MS of the constraining portion 3 is defined by the assembly or union of the first cross-section FS of the core or main body 5, which constitutes the resistant section of the constraining portion 3, with the second cross-section SS of the complementary or filling structure and/or volume 6, if present.

Figure 1:
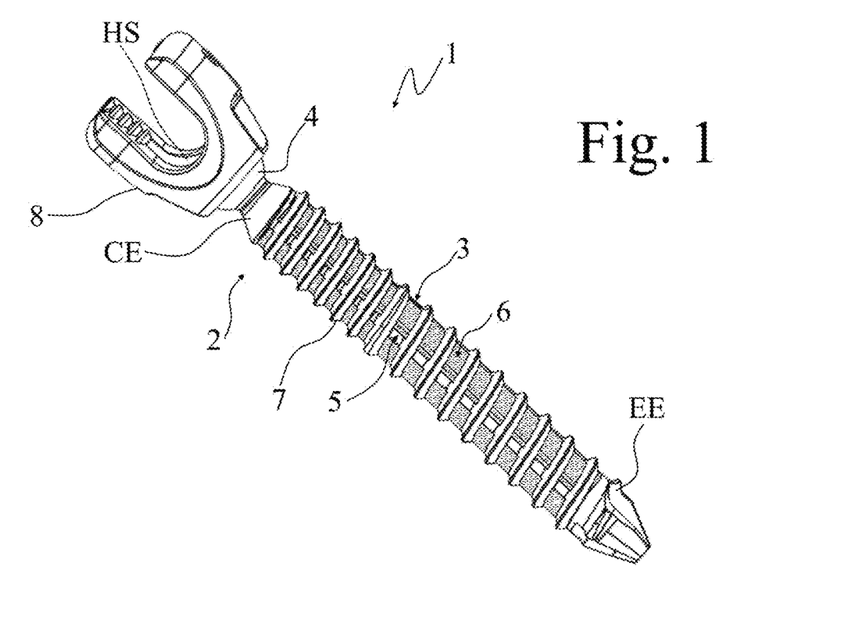
FIG. 1 is a perspective view of a fixing device according to an embodiment of the present invention.
Figure 2:
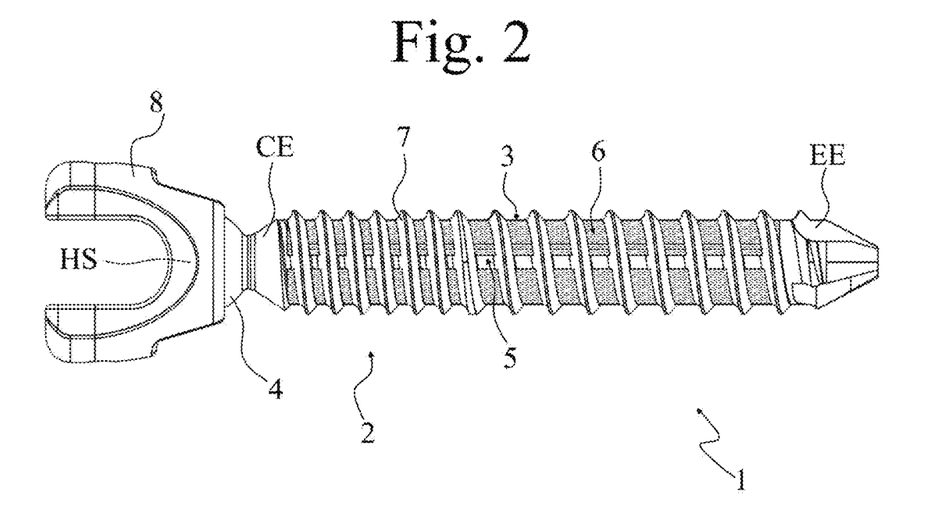
FIG. 2 is a side view of the fixing device according to the embodiment shown in FIG. 1.
Figure 3:
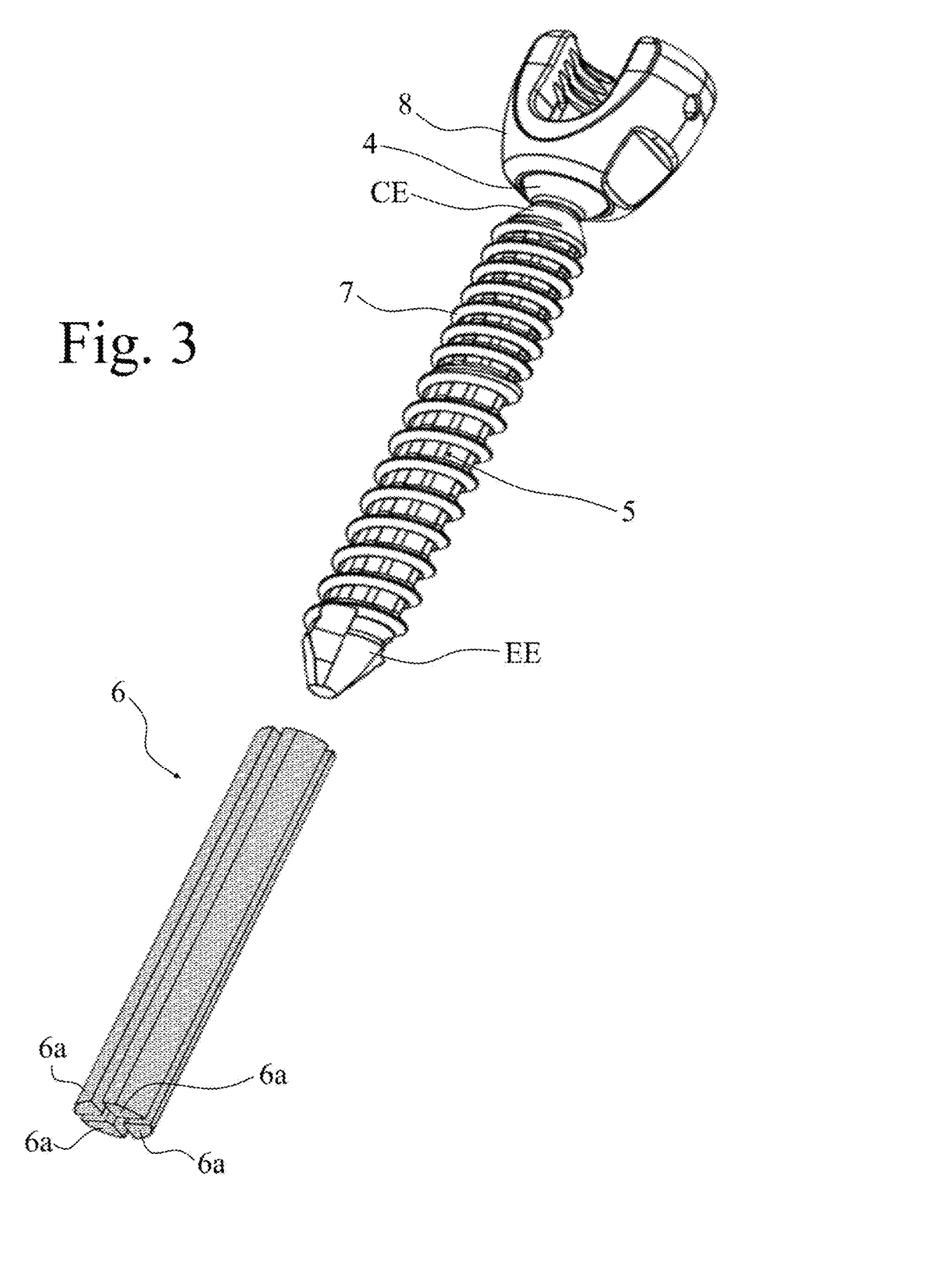
FIG. 3 is an exploded view of the fixing device according to the embodiment shown in FIG. 1.

According to the non-limiting embodiment of the present invention shown in FIG. 1, the overall cross-section MS of the constraint portion 3 is of circular configuration.

The cross-section of the anchoring body 2 and/or of the fixing device 1 has a conformation substantially corresponding to the overall cross-section MS.

The fixing device 1 according to the present invention provides that the complementary or filling structure and/or volume 6 comprises or consists of at least two portions 6a.

Similarly, the core or main body 5 comprises at least a central portion 5a and at least two protruding or projecting portions 5b extending from the central portion 5a, for example towards the outside of the fixing device 1.

In at least one version, the central portion 5a is coaxial to the anchoring body 2 and/or to the constraint portion 3 and/or to the fixing device 1.

The protruding or projecting portions 5b define with the central portion 5a respective housing or containment areas or spaces HA for the at least two portions 6a of the complementary or filling structure and/or volume 6.

It should be considered that, preferably, both the at least one central portion 5a and the at least two protruding or projecting sections 5b extend—as regards one of their dimensions, for example, greater—along the longitudinal development of the constraint portion 3 or, more particularly, of the core or main body 5.

Furthermore, the at least two protruding or projecting portions 5b can both have a straight or curved or at least partially curved design or, alternatively, a protruding or projecting portion 5b can have a curved or at least partially curved design and the other protruding or projecting portion 5b can be straight.

Preferably, the core or main body 5 is full, i.e. not hollow or in any case completely full.

Figure 13:
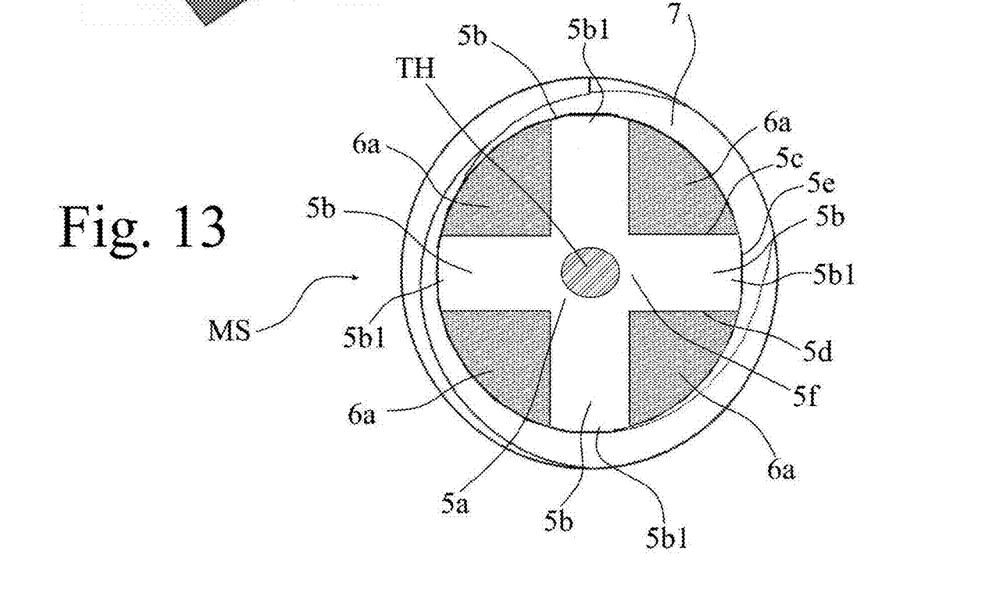
FIG. 13 is a cross-sectional view of the fixing device according to another embodiment of the present invention.

Moreover, according to the non-limiting embodiment shown in FIG. 13, the core or main body 5 can have a longitudinal through hole TH, for example a circular longitudinal through hole TH.

Preferably, the longitudinal through hole TH extends for the entire longitudinal extension of the fixing device 1, if desired, of the constraint portion 3 or of the core or main body 5.

As can be understood, with this configuration the fixing device 1 can advantageously also be used as a cannulated screw.

According to other non-limiting examples of the present invention, the longitudinal through hole TH could extend only partially along the longitudinal extension of the fixing device 1, if desired of the constraint portion 3 or the core or main body 5, for example, starting from the distal end CE towards the apical engaging end EE or vice versa, between 40% and 90%, for example for 65% of its longitudinal development.

Furthermore, it should be considered that, if a longitudinal through hole TH is provided as described above, it is preferable to increase the volume of the core or main body 5 with respect to that of the complementary or filling structure and/or volume 6, for example by a percentage included between 10% and 30%, if desired depending on the width of the longitudinal through hole TH, so as to eliminate or in any case mitigate the reduction in mechanical strength of the fixing device 1 generated by the presence of the longitudinal through hole TH.

With reference by way of example and not of limitation to the overall cross-section MS of the constraint portion 3 or to the cross-section FS, each protruding or projecting portion 5b has a shape and/or a cross-section (considered along a transverse or perpendicular plane with respect to the first direction or longitudinal direction of such portions) substantially rectangular or square or trapezoidal or triangular or polygonal, and/or with some or all rounded edges, etc.

Figures 7, 8, 9:
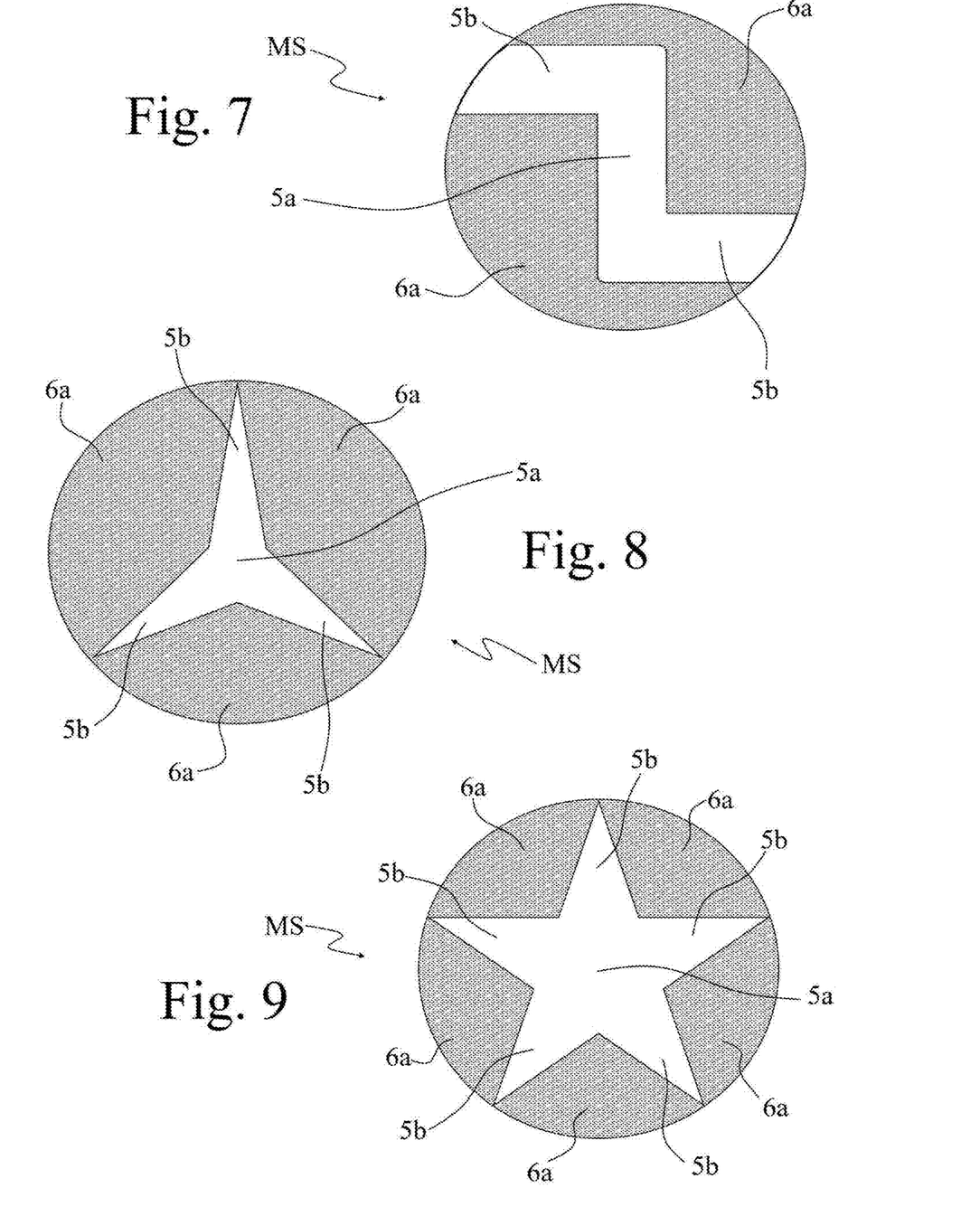

Further non-limiting embodiments are shown, as well as in FIG. 4, also in FIGS. 7 to 9.

In particular, by way of example, each protruding or projecting portions 5b can comprise a first segment 5c, a second segment 5d and a connecting segment 5e for the first segment 5c and the second segment 5d.

Each of the first segment 5c, second segment 5d and connecting segment 5e can be a straight, curved or at least partially curved segment.

In at least one version of the invention, the first segment 5c is substantially parallel to the second segment 5d and/or the third connecting segment 5e is perpendicular to the first segment 5c and/or to the second segment 5d.

In at least one version of the invention, the first segment 5c and/or the second segment 5d has a larger size than the third connecting segment 5e.

In a still further version, the first segment 5c and the second segment 5d substantially have the same length.

In a version of the invention, for example illustrated in FIG. 4, the core or main body has a cross-section in the shape of a cross, in which there are four protruding or projecting portions 5b, perpendicular to each other.

Preferably, at least the first segment 5c and/or at least the second segment 5d of at least one protruding or projecting portion 5b, more preferably each first segment 5c and each second segment 5d of each protruding or projecting portion 5b, has a connecting end 5f of the latter with the central portion 5a with at least partially curved or in any case tapered design, for example so as not to form unwanted edges, points or undercuts.

Preferably, the anchoring body 2 or, more particularly, the constraint portion 3 comprises at least one thread 7, so as to facilitate the engagement or grafting of the fixing device 1, in use, in the respective bone seat.

Advantageously, the at least one thread 7 extends concentrically along the longitudinal extension of the constraint portion 3, if desired with a variable pitch, for example progressively decreasing along the longitudinal extension of the constraint portion in the direction of approaching the head portion 4, thus to facilitate the engagement of the fixing device 1 in a respective bone seat.

For example, the thread 7 consists of a helical or spiral coil structure, which wraps the constraint portion 3. Each coil is spatially separated, along a longitudinal direction, with respect to a further or subsequent coil. Therefore, between one coil and the other of the thread 7 there is the complementary or filling structure and/or volume 6 which is visible and/or capable of coming into contact, in use, with the tissue of the bone site in which the fixation device 1 is implanted.

Moreover, at least one, preferably each, of the at least two protruding or projecting portions 5b can advantageously comprise a support or connection end 5b1 for or with the at least one thread 7.

In at least one version of the invention, this support or connection end 5b1 for or with the at least one thread 7 corresponds to the connecting segment 5e.

Therefore, in essence, the thread 7 is attached or supported or constrained to the at least two protruding or projecting portions 5b and/or to the support or connection end 5b1 and/or to the connecting segment 5e of said at least two protruding or projecting portions 5b.

In this regard, the housing or containment areas or spaces HA of the at least two complementary or filling portions 6a can be defined, in addition to the central portion 5a and the at least two protruding or projecting portions 5b, also by the at least one thread 7.

In this case, the central portion 5a, the at least two protruding or projecting portions 5b and the at least one thread 7 can define each or at least one housing or containment area or space HA as a housing or containment cage of a respective complementary or filling portion 6a.

In the case in which the at least one thread 7 is supported or connected by or with the support or connection end 5b1 of at least one or each protruding or projecting portion 5b, it acquires a considerable solidity and resistance as it is able to discharge, on at least one or each protruding or projecting portion 5b, the mechanical stresses generated by the coupling of the fixing device 1.

Advantageously, the at least one thread 7 can be made in one piece with the core or main body 5 and/or with said complementary or filling structure and/or volume 6, if desired also in the same material, through methods that will be described below in more detail.

According to a non-limiting example of the present invention, each complementary or filling portion 6a (they are four in FIG. 5) has a cross-section with a circular sector shape, for example with a circular sector shape equal to a quarter of a circle. In this way, this section completes, with the section FS of the core or main body 5, the overall cross-section MS of the constraint portion 3. The latter, as can be seen in the example of FIG. 6, is therefore overall circular.

Any conformations can be provided, as can be seen from FIGS. 7 to 9, in which the cross-section of each portion 6a of the complementary or filling volume 6 can correspond to a circular sector that defines an angle greater than 90°, or less than 90°, in other words greater or less than a quarter of a circle, or quadrangular, or "L"-, or "S"-shaped, or irregular as shown in FIG. 7.

The core or main body 5 is structurally more resistant to mechanical stresses, for reasons which will be detailed below.

Returning, in general, to the structure of the constraint portion 3, it is preferably designed and manufactured so that the surface bulk of the first and second cross-sections FS, SS with respect to the overall cross-section MS are selected by optimizing the mechanical strength of the fixing device 1, which varies according to the configuration and the surface occupied by the core or main body 5, and the osseointegration capacity of the fixing device 1, which varies according to the surface occupied by the complementary or filling structure and/or volume 6.

It should be noted that, in the previous paragraph, reference was made to the surface bulk because reference was made to cross-sections, however, the bulk can also be clearly defined by volumetric terms, as both the core or main body 5 and the complementary or filling structure and/or volume 6 preferably extend along the longitudinal development of the constraint portion 3 and, therefore, define a three-dimensional or volumetric bulk.

The mechanical strength of the fixing device 1 can be considered and evaluated as its resistance to torsion and bending when subjected to a given test load.

In particular, considering a given configuration of the core or main body 5, the mechanical resistance is proportional to the volume of this core or main body 5.

Similarly, also the osseointegration capacity of the fixing device 1, which can be considered and evaluated as its ability to integrate into the complementary or filling structure and/or volume 6 the possible bone tissue of the bone site in which it is, in use, engaged, is directly proportional to the porosity of the complementary or filling volume 6.

Advantageously, the fixing device 1 optimizes the volume occupied by the core or main body 5, the complementary or filling volume 6 and its porosity, so as to obtain the best compromise between mechanical strength and osseointegration capacity of the fixing device 1.

Preferably, the complementary or filling structure and/or volume 6 has a porosity between 40% and 80%.

Preferably, the second cross-section SS has a surface bulk between 25% and 65%, for example equal to 35% or 45% with respect to the surface of the overall cross-section MS, or, similarly, the volume of the complementary or filling structure and/or volume 6 is between 25% and 65%, for example equal to 35% or 45% of the volume of the constraint portion 3.

From a manufacturing point of view, the core or main body 5 can be made of metallic material, for example of titanium, titanium alloys, steel, if desired, stainless, or of polymeric material, if desired, biocompatible.

Similarly, the complementary or filling structure and/or volume 6 can also be made of metallic material, for example titanium, titanium alloys, magnesium alloys, tantalum alloys, stainless steel, or of a polymeric material, for example polylactic, or in ceramic material, for example hydroxyapatite or brushite.

Clearly, different embodiment combinations can also be provided between core or main body 5 and complementary or filling structure and/or volume 6, for example a core or main body 5 made of titanium and a complementary or filling volume 6 made of hydroxyapatite.

Alternatively, different materials can also be provided for each complementary or filling portion 6a of the complementary or filling structure and/or volume 6, for example a complementary or filling portion 6a in hydroxyapatite and another complementary or filling portion 6a in titanium, and so on.

With reference to the non-limiting example of the overall cross-section MS of the constraint portion 3 shown in FIG. 7, the core or main body 5 comprises two protruding or projecting portions 5b which rise from the central portion 5a, for example from the ends of this the latter, for example in a perpendicular or inclined manner with respect to the direction of the central portion 5a.

In this version, both the central portion 5a and each protruding or projecting portion 5b have a cross-section (considered along a transverse or perpendicular plane with respect to the longitudinal direction or first dimension of these sections) that is substantially rectangular or square or trapezoidal or triangular or polygonal, and/or with rounded edges, etc.

Preferably, the core or main body 5 comprises three or five protruding or projecting portions 5b, which rise from the central portion 5a, arranged so that the first cross-section FS is shaped like a sunburst or star, for example with 3 or 5 points, such as shown in FIGS. 8 and 9 respectively.

The configuration of the core or main body 5 with four protruding or projecting portions 5b arranged as a cross is that which allows to obtain the best compromise and the best optimization between the volume or the surface in cross-section occupied by the core or main body 5 and the volume or surface in cross-section occupied by the complementary or filling structure and/or volume 6, and, consequently, the best compromise and the best optimization between the mechanical strength and the osseointegration capacity of the fixing device 1.

Considering, by way of non-limiting example, the configuration of the core or main body comprising four protruding or projecting portions 5b arranged as a cross, an overall circular cross-section MS with a diameter of about 10 mm, a construction material having a tensile strength or $R_m$ equal to about 860 MPa as well as a yield strength or $R_{p0.2}$ equal to about 790 MPa, the application of a torsional load equal to about 12 Nm generates a maximum critical value equal to about 147 MPa and therefore well below the limit values of $R_m$ and $R_{p0.2}$ mentioned above.

Therefore, it should be considered that the configuration just described is very robust to mechanical stresses but, at the same time, it allows to use a considerable volume for the complementary or filling structure and/or volume 6, in fact, obtaining a large osseointegration capacity of the fixing device 1.

As can be understood, on the other hand, the configuration of the core or main body 5 with two or three protruding or projecting portions 5b further rewards the osseointegration capacity of the fixing device 1, however, decreasing its mechanical strength, since the percentage of volume occupied by the complementary or filling structure and/or volume 6 is greater than the volume it would occupy in a constraint portion 3 of the same configuration but with a core or main body 5 comprising four protruding or projecting portions 5b arranged in a cross or star shape, considering that the thickness or volume of the protruding or projecting portions 5b is the same for both configurations.

On the contrary, the configuration of the core or main body 5 with five or more protruding or projecting portions 5b further rewards the mechanical strength of the fixing device 1, however, decreasing its osseointegration capacity, since the percentage of volume occupied by the complementary or filling structure and/or volume 6 is smaller than the volume it would occupy in a constraint portion 3 of the same configuration but with a core or main body 5 comprising four protruding or projecting portions 5b arranged in a cross or star shape, considering that the thickness or volume of the protruding or projecting portions 5b is the same for both configurations.

It should be noted that, in the case of a configuration of the core or main body 5 comprising protruding or projecting portions 5b arranged so that the first cross-section FS is cross- or star-shaped, these protruding or projecting portions 5b can also be curved or at least partially curved.

As regards the complementary or filling structure and/or volume 6 or, more particularly, the at least two complementary or filling portions 6a, they are advantageously configured on the basis of the first cross-section FS of the core or main body 5.

In other words, the at least two complementary or filling portions 6a can be configured so as to fill the respective housing or containment areas or spaces HA defined by the at least one central portion 5a, by the at least two protruding or projecting portions 5b and, if present from the at least one thread 7.

Figure 10:
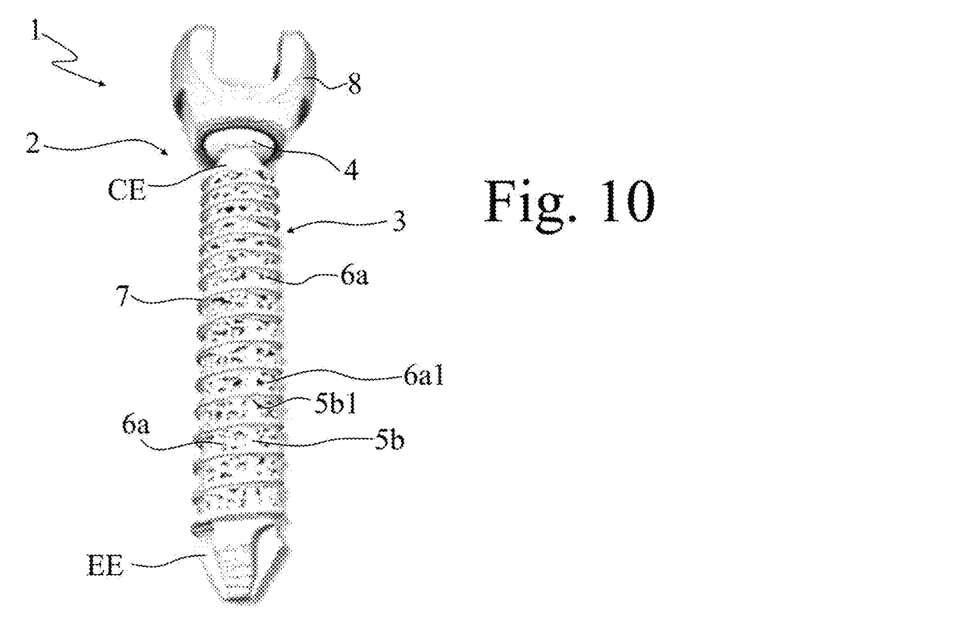
FIGS. 10 and 11 show respectively a front and perspective view of a fixing device according to the embodiment shown in FIG. 1 obtained through a three-dimensional or 3D printing method.
Figure 11:
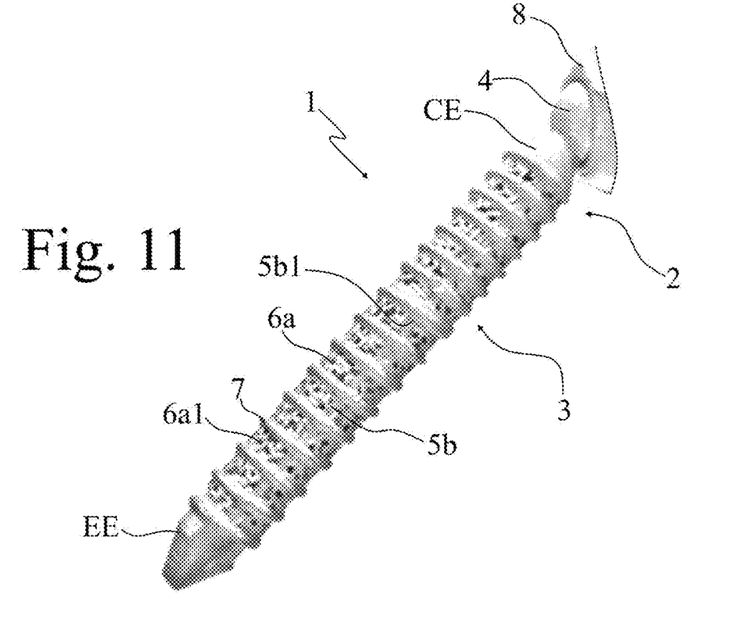

According to a non-limiting embodiment of the present invention shown in FIGS. 10 and 11, the complementary or filling structure 6 comprises a porous and/or trabecular structure and/or with pores or cavities.

This trabecular structure is defined by a plurality of trabeculae, that is to say a plurality of microscopic lamellar units that delimit respective cavities, if desired intercommunicating, for example arranged in a disordered or regular way, designed to allow the integration in them of the bone tissue present at the insertion seat of the fixing device 1.

Advantageously, the complementary or filling structure and/or volume 6 can be made in one piece with the core or main body 5, by means of methods which will be described in more detail below.

Alternatively and according to another non-limiting embodiment of the present invention, the complementary or filling structure and/or volume 6 or, more particularly, the at least two complementary or filling portions 6a, could be inserted, for example by injection or positioning, in the respective housing or containment areas or spaces HA after the realization of the core or main body 5.

From a structural point of view, the fixing device 1 and/or the anchoring body 2 can comprise—as anticipated above—an apical engagement end EE, if desired shaped like a tip, configured to engage in a respective bone seat.

The apical engagement end EE is opposite to the head portion 4.

The apical engaging end EE, in at least one version of the invention, has a substantially conical or truncated conical or pyramidal or truncated pyramid or prismatic or diamond shape, and/or with grooves or ridges, etc.

Preferably, the apical engaging end EE at least partially comprises a porous structure or surface designed to facilitate, in use, the adaptation or integration of the bone tissue with the fixing device 1. Possibly, this porosity can be constituted by a cellular structure, regular or irregular, and/or comprising pores or cavities.

Alternatively, the apical engaging end EE can be full and/or solid or in any case non-porous.

According to the non-limiting embodiment of the present invention shown in FIGS. 10 and 11, the apical engaging end EE is made in one piece with the core or main body 5.

Still from a structural point of view, the fixing device 1 and/or the anchoring body 2 can comprise the end CE, distal from the apical engaging end EE, for connection with the head portion 4.

As regards the head portion 4, it can advantageously be made in one piece with an anchoring body 2 and/or with the distal end CE.

The distal end CE, in at least one version of the invention, has a substantially conical or truncated conical or pyramidal or truncated pyramid or discoidal or flat conformation (as, for example, illustrated in FIG. 12), etc.

According to the non-limiting embodiment of the present invention shown in FIG. 1, the head portion 4 is substantially spherical or semi-spherical.

According to other non-limiting embodiments of the present invention, the head portion 4 could also have other configurations, for example pyramidal, prismatic, discoidal, cylindrical or, more generally, of an irregular shape.

Advantageously, the head portion 4 can delimit, at its own distal end with respect to the constraint portion 3, a suitable engagement seat 12 (for example illustrated in FIG. 12) intended to allow the coupling or tightening of the fixing device 1 by means of a suitable tool, such as for example a screwdriver or the like.

If desired, the fixing device 1 or, more particularly, the anchoring body 2 can comprise a connection component 8, operatively associated or associable, in use, with the head portion 4, designed to allow the connection, by means of suitable connection means, of further devices to said fixing device 1.

In this regard, according to the non-limiting embodiment of the present invention shown in FIG. 1, the head portion 4 is operatively associated in a rotational manner with the connection component 8 through a ball joint coupling. In this case, the head portion advantageously has a spherical or semi-spherical conformation and the fixing device 1 consists of a pedicle screw.

In this regard, the head portion 4, substantially spherical or semi-spherical, is housed in a suitable housing seat HS defined in the connection component 8.

Alternatively, the connection component 8 can comprise a substantially spherical or semi-spherical configured portion, so as to be housed in a suitable housing seat defined in the head portion 4, the latter having any shape, so as to form the coupling ball joint.

This coupling is particularly advantageous in that it allows both an inclination and a rotation of the connection component 8 with respect to a longitudinal axis of the anchoring body 2, thus being able to adjust its position and being very versatile when it is necessary to associate additional components or devices with the fixing device 1.

If the fixing device 1 is a pedicle screw, the connection component 8 can advantageously be configured as a "U" and/or tulip-shaped element, so as to allow the operative connection thereto of further devices, such as for example other fixing devices 1, for example by means of suitable metal elements, if desired metal bars or plates.

According to the non-limiting embodiment of the present invention shown in FIGS. 10 and 11, the fixing device 1 is made by means of a method, described in more detail below, which allows to obtain a connection component 8 already associated or assembled to the anchoring body 2. In this way, it is possible to avoid any clinical disassembly problems linked to the fact of having the connection component 8 initially separated from the anchoring body 2 and assembled to it at a later time.

Furthermore, the connection component 8 can comprise a volume and/or a surface at least partially porous, trabecular, consisting of cells with a regular or irregular pattern, or full.

The fixing device 1 is preferably obtained by means of a three-dimensional or 3D printing method, even more preferably, by means of additive manufacturing.

This method allows, through an appropriate positioning of the supports for the realization of the fixing device 1, together with a suitable digital design of the latter, for example to obtain in a single process the anchoring body 2 and the connection component 8 already assembled, when the latter is present.

Moreover, this additive manufacturing methodology allows the fixing device 1 to be realized in an optimal way, for example through a multi-layer fabrication, even when the complementary or filling structure and/or volume 6 thereof comprises a geometrically very complex porous surface or a structure, such as a porous or trabecular structure.

According to other non-limiting embodiments of the present invention, only some components of the fixing device 1 could be made by a three-dimensional or 3D printing method, if desired by additive manufacturing, and only successively be assembled with the remaining components that constitute the fixing device 1.

Thus, for example, an anchoring body 2 could be provided with a constraint portion 3 comprising a core or main body 5 made through the additive manufacturing methodology and a complementary or filling structure or volume 6 inserted, or injected or positioned, subsequently, in the respective housing or containment areas or spaces HA.

Alternatively, it could be the complementary or filling structure and/or volume 6 to be made by means of the additive manufacturing methodology and then be inserted or constrained with an anchoring body 2 made separately by means of a different method.

A non-limiting example of use of the fixing device 1 according to the non-limiting embodiment of the present invention shown in FIGS. 10 and 11 is described below.

Assuming, by way of example, that the fixing device 1 is a pedicle screw used in the field of vertebral surgery, the surgeon can insert the fixing device 1 into the bone site of interest.

The core or main body 5, thanks to the first cross-section FS optimized by the cross or star configuration, is able to easily withstand the stresses generated by the insertion of the fixing device 1 in the bone seat.

In the same way, the thread 7, supported by or connected to the respective supporting or connecting ends 5b1 of the protruding or projecting portions 5b allows, in addition to easier insertion, also a better overall mechanical strength of the fixing device 1.

Moreover, thanks to the ball joint coupling between the head portion 4 and the connection component 8, the surgeon can easily adjust the inclination of the latter so as to connect to it, as needed, other fixing devices 1 by means of suitable connective bars or plates.

Once inserted, the fixing device 1 allows, thanks to the high volume occupied by the complementary or filling structure and/or volume 6 or, more particularly, by the trabecular structure, a considerable improvement in the osseointegration capacity of the bone tissue present in the bone implant site.

In this regard, the external accessibility of the trabecular structure allows a continuous wetting of the same with the biological fluids necessary for the growth of the bone tissue inside the cavities defined therein.

As it can be understood, having a greater volume of trabecular structure available, the integration of the bone tissue is deeper, strong and effective, giving further fixation and stabilization of the fixing device, with a consequent increase in resistance to stress.

The fixing device 1 according to the present invention has characteristics of high mechanical resistance to torsion and bending and, at the same time, allows the use of a greater volume of material useful for the adaptation or integration of the bone tissue, which allows a better osseointegration when compared to the fixing devices of same sizes produced according to the prior art.

This is achieved by optimizing the first cross-section FS of the core or main body 5, i.e. its configuration and its dimensions given a particular overall cross-section MS of the constraint portion 3, as a function of the mechanical strength and volume of material to be used for bone tissue adaptation or integration.

If the fixing device 1 is used, for example, in the field of vertebral surgery as a pedicle screw, these characteristics of mechanical strength and optimized osseointegration allow to significantly improve and speed up the post-operative recovery of the patient.

Moreover, the fixing device 1 can also be obtained through a single manufacturing step by means of a three-dimensional or 3D printing method, such as additive manufacturing, so as to avoid complicated assembly operations and being able to obtain complex components from a structural point of view, such as for example a porous or trabecular structure.

It has thus been seen that the invention fully achieves the proposed arms.

Modifications and variants of the invention are possible within the scope of protection defined by the claims.

The invention claimed is:

1. A fixing device, comprising:
   an anchoring body including a constraint portion, engageable, in use, in a respective bone seat, and extending along a first direction or longitudinal direction, and a head portion, said constraint portion having an overall cross-section and comprising a core or main body comprising at least a central portion and at least two protruding or projecting portions extending from said central portion, said core or main body delimiting a first cross-section,
   wherein said at least two protruding or projecting portions define with said central portion respective housing or containment areas or spaces,
   wherein said constraint portion further comprises a complementary or filling structure, placed or housed in said housing or containment areas or spaces, delimiting a second cross-section which defines, with said first cross-section, said overall cross-section of said constraint portion, wherein said complementary or filling structure comprises a porous or trabecular structure, and
   wherein said fixing device, including said filling structure, is made of metallic material,
   wherein said second cross-section has an extent between 25% and 65% with respect to the extent of said overall cross-section, and
   wherein said constraint portion has an apical engaging end and a distal end, said distal end being connected to said head portion, wherein said porous or trabecular structure is present from said apical engaging end to said distal end.

2. The fixing device according to claim 1, wherein said complementary or filling structure comprises at least two complementary or filling portions.

3. The fixing device according to claim 1, wherein said complementary or filling structure has a porosity comprised between 40% and 80%.

4. The fixing device according to claim 3, wherein said complementary or filling structure comprises a trabecular structure designed to allow the integration of the bone tissue.

5. The fixing device according to claim 1, wherein said fixing device is made of metallic material, including titanium, titanium alloys, magnesium alloys, tantalum alloys, stainless steel, or polymeric biocompatible material, or ceramic material.

6. The fixing device according to claim 1, wherein the relative extents of said first and said second cross-section with respect to said overall cross-section is selected by optimizing the mechanical strength of said fixing device, which varies according to the configuration and extent of said core or main body, and the osseointegration capacity of said fixing device, which varies according to the configuration and extent of said complementary or filling structure and/or volume.

7. The fixing device according to claim 1, wherein said at least two protruding or projecting portions are three, four, five or more and are arranged so that said first cross-section is cross or star or sunburst shaped.

8. The fixing device according to claim 1, wherein said anchoring body comprises at least one thread, and at least one of said protruding or projecting portions comprises a supporting or connecting end for or with said thread.

9. The fixing device according to claim 8, wherein said at least one thread is made in one single continuous piece with said complementary or filling structure and with said core or main body.

10. The fixing device according to claim 8, wherein each housing or containment area or space is defined, as well as by said central portion and by said at least two protruding or projecting portions, also by said thread.

11. The fixing device according to claim 8, wherein said thread extends concentrically along the longitudinal development of said constraint portion and wherein said thread extends with a variable pitch so as to facilitate engagement of said fixing device in a respective bone site.

12. The fixing device according to claim 1, comprising a connection component, operatively associated or associable, in use, with said head portion, designed to allow the connection, by means of suitable connection means, of further devices to said fixing device.

13. The fixing device according to claim 12, wherein said head portion is operatively associated in a rotational manner with said connection component through a ball joint coupling.

14. The fixing device according to claim 12, wherein said connection component is shaped as a "U" or tulip shaped element.

15. The fixing device according to claim 1, wherein said anchoring body comprises an apical engaging end, opposite to said head portion, shaped like a tip and designed to engage in a respective bone seat.

16. The fixing device according to claim 15, wherein said apical engaging end at least partially comprises a porous or trabecular structure or surface designed to facilitate, in use, the adaptation or integration of the bone tissue with said fixing device.

17. The fixing device according to claim 1, wherein said fixing device is a pedicle screw or a bone screw.

18. The fixing device according to claim 1, wherein at least a protruding or projecting portion comprises a first segment and a second segment, in which at least said first segment and/or at least said second segment of said protruding or projecting portion has a connecting end of said protruding or projecting portion with said central portion having an at least partially curved or tapered design.

19. The fixing device according to claim 1, obtained by means of a three-dimensional or 3D printing method or by means of an additive manufacturing technique.

20. A method for making a fixing device, comprising an anchoring body including a constraint portion, engageable, in use, in a respective bone seat, and extending along a first direction or longitudinal direction, and a head portion, said constraint portion being provided with an overall cross-section and including a core or main body delimiting a first cross-section, in which said core or main body comprises at least a central portion and at least two protruding or projecting portion extending from said central portion, wherein said at least two protruding or projecting portions define with said central portion respective housing or containment areas or spaces,
   wherein said fixing device comprises a complementary or filling structure, placed or housed in said housing or containment areas or spaces, and delimiting a second cross-section which defines, with said first cross-section, said overall cross-section of said constraint portion,
   wherein said complementary or filling structure comprises a porous or trabecular structure,
   wherein said fixing device, including said filling structure, is made of metallic material,
   wherein said constraint portion has an apical engaging end and a distal end, said distal end being connected to said head portion, wherein said porous or trabecular structure is present from said apical engaging end to said distal end, and
   wherein said method comprises making said fixing device by three-dimensional or 3D printing or by an additive manufacturing technique through a single manufacturing step.

21. A fixing device, comprising:
an anchoring body including a constraint portion engageable, in use, in a respective bone seat, and extending along a first direction or longitudinal direction, said constraint portion having an apical engaging end and a distal end, said distal end connected to a head portion;
said constraint portion having an overall cross-section and comprising a core or main body comprising at least a central portion and at least two protruding or projecting portions extending from said central portion,
wherein said at least two protruding or projecting portions define with said central portion respective housing or containment areas or spaces, wherein each of said at least two protruding or projecting portions comprises a support or connection end,
wherein said constraint portion further comprises a complementary or filling structure, placed or housed in said housing or containment areas or spaces, delimiting a second cross-section which defines, with a first cross-section, said overall cross-section of said constraint portion,
wherein said complementary or filling structure comprises a porous or trabecular structure,
wherein said fixing device, including said filling structure, is made of metallic material,
wherein said distal end is connected to said head portion and wherein said porous or trabecular structure is present from said apical engaging end to said distal end, and
wherein said anchoring body further comprises at least one continuous thread attached to each of said support or connection ends, wherein said at least one continuous thread comprises an uninterrupted helical or spiral coil structure which runs from the head portion to the apical engaging end and wraps around both the core or main body and the complementary or filling structure.

* * * * *